(12) United States Patent
Kertser et al.

(10) Patent No.: US 11,510,591 B2
(45) Date of Patent: Nov. 29, 2022

(54) CAPNOGRAPHY SYSTEMS WITH INDICATOR LIGHTS

(71) Applicant: Oridion Medical 1987 Ltd., Jerusalem (IL)

(72) Inventors: Michael Kertser, Bney Aish (IL); Tzvika Lefkovits, Giva'at Zeev (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 486 days.

(21) Appl. No.: 16/032,173

(22) Filed: Jul. 11, 2018

(65) Prior Publication Data

US 2020/0015706 A1 Jan. 16, 2020

(51) Int. Cl.
| | |
|---|---|
| *A61B 5/08* | (2006.01) |
| *A61B 5/00* | (2006.01) |
| *A61B 5/097* | (2006.01) |
| *A61M 16/06* | (2006.01) |
| *G01N 33/497* | (2006.01) |

(52) U.S. Cl.
CPC ............ *A61B 5/082* (2013.01); *A61B 5/0082* (2013.01); *A61B 5/097* (2013.01); *A61M 16/0666* (2013.01); *G01N 33/497* (2013.01); *A61M 2230/432* (2013.01)

(58) Field of Classification Search
CPC .................. A61B 5/082; A61B 5/083–5/0836
See application file for complete search history.

(56) References Cited

U.S. PATENT DOCUMENTS

| | | | |
|---|---|---|---|
| 2002/0112730 A1* | 8/2002 | Dutkiewicz | A61M 16/085 128/207.18 |
| 2007/0093725 A1 | 4/2007 | Shaw | |
| 2008/0039735 A1 | 2/2008 | Hickerson | |
| 2009/0118632 A1* | 5/2009 | Goepp | A61B 5/0836 600/532 |
| 2010/0286607 A1* | 11/2010 | Saltzstein | A61B 5/02055 604/93.01 |
| 2010/0305464 A1 | 12/2010 | Ratner | |
| 2013/0123579 A1* | 5/2013 | Adams | A61B 90/90 600/117 |
| 2013/0204099 A1* | 8/2013 | Colman | A61B 5/0816 600/301 |
| 2015/0040896 A1* | 2/2015 | Chodkowski | A61M 16/021 128/202.22 |
| 2015/0190088 A1* | 7/2015 | Chen | A61B 5/02055 600/301 |

(Continued)

OTHER PUBLICATIONS

Jaffe, Michael B. "Volumetric Capnography—The Next Advance in CO2 Monitoring." 2015. 9 pages. (Year: 2015).*

(Continued)

*Primary Examiner* — Meredith Weare
(74) *Attorney, Agent, or Firm* — Cantor Colburn LLP (57) ABSTRACT

Disclosed herein are systems and methods for producing an illumination pattern in a gas tube of a facially-fitting device, which is used in conjunction with a capnograph. The illumination pattern is determined by at least one illumination parameter, derived at least from measured $CO_2$ data, such that the illumination pattern is indicative of at least one breath-related/physiological parameter and/or one or more of the respiratory/physiological conditions determined/assessed based at least on the $CO_2$ data.

19 Claims, 3 Drawing Sheets

(56) References Cited

U.S. PATENT DOCUMENTS

2015/0265828 A1* 9/2015 Colman ................ F16L 21/00
                                                       604/535
2017/0266399 A1  9/2017 Campana et al.
2019/0365281 A1* 12/2019 Orr ....................... A61B 5/746
2020/0009344 A1*  1/2020 Kertser ................ A61M 16/06

OTHER PUBLICATIONS

International Application No. PCT/IL2019/050756 International Search Report and Written Opinion dated Sep. 13, 2019, 12 pages.

* cited by examiner

CAPNOGRAPHY SYSTEMS WITH INDICATOR LIGHTS

TECHNICAL FIELD

The present disclosure relates generally to breath sampling.

BACKGROUND

Breath sampling is often performed to monitor the health and well-being of a subject. A capnograph is used to monitor $CO_2$ levels in exhaled breath of a subject. Based on the $CO_2$ levels, breath-related parameters of the subject may be determined, and a respiratory status thereof may be assessed, as well as physiological conditions.

SUMMARY

Aspects of the disclosure, according to some embodiments thereof, relate generally to breath sampling analyzers, such as capnographs. More specifically, but not exclusively, aspects of the disclosure, according to some embodiments thereof, relate to capnography systems with indicator lights.

The present disclosure, according to some aspects thereof, provides breath sampling analyzers, such as capnographs, including an illumination source(s) (e.g. an LED or LED array) configured to produce an illumination pattern in a gas tube (e.g. a light beam guided along the gas tube and visible from outside the gas tube) of a facially-fitting device, such as a nasal cannula. The illumination pattern may be configured to provide medical personnel with visual information regarding breath-related parameters of the subject, respiratory status thereof, and/or physiological conditions thereof (beyond the respiratory status). Advantageously, the visual information may be presented in a simplified manner (e.g. as compared to a capnogram), for example, the intensity of the light beam may be correlated to the respiration rate of the subject. According to some embodiments, the illumination pattern may also function to signal incorrect placement of the facially-fitting device.

The present disclosure, according to other aspects thereof, provides an illuminating connector configured to be connected, on one end thereof, to a gas port of a breath sampling analyzer, such as a capnograph, and, on the second end thereof, to a gas tube of a facially fitting device. The connector includes an illumination module configured to produce an illumination pattern in a gas tube of the facially-fitting device. The illumination pattern may be configured to provide medical personnel with clearly and simply presented visual information regarding breath-related/physiological parameters of the subject, respiratory status thereof, and/or physiological conditions thereof. According to some embodiments, the illumination pattern may also function to signal incorrect fitting of the facially-fitting device. Advantageously, according to some embodiments, the connector may be configured to be used with commercially available breath sampling analyzers, such as capnographs.

The present disclosure, according to other aspects thereof, provides a disposable breath-sampling assembly (e.g. a nasal cannula) including a facially-fitting member, for collecting exhaled breath of a subject, and a gas tube connected to the facially-fitting member on one end thereof, and configured to be connected, on a second end thereof, to a gas port of a breath sampling analyzer, such as a capnograph. The gas tube is configured to convey the exhaled breath of the subject to the capnograph. The breath-sampling assembly includes an illumination module configured to produce an illumination pattern in the gas tube. The illumination pattern may be configured to provide medical personnel with clearly and simply presented visual information regarding breath-related/physiological parameters of the subject, respiratory status thereof, and/or physiological conditions thereof. According to some embodiments, the illumination pattern may also function to signal incorrect fitting of the facially-fitting member on the face of a subject. Advantageously, according to some embodiments, the breath sample assembly may be configured to be used with commercially available capnographs.

Thus, according to an aspect of some embodiments, there is provided a breath sampling analyzer, such as a capnograph for use in conjunction with a facially-fitting device for exhaled breath sampling. The capnograph includes:

A $CO_2$ sensing arrangement configured to receive, via a gas tube fluidly connected to a facially-fitting device, exhaled breath from a subject monitored by the capnograph.

A control unit configured to process $CO_2$ sensing data, received from the $CO_2$ sensing arrangement, and to determine independently or together with an external agent, at least one breath-related/physiological parameter of the subject and/or assess one or more respiratory/physiological conditions thereof based at least on the $CO_2$ sensing data.

An illumination module including an illumination source and configured to be associated with the gas tube and to produce an illumination pattern in the gas tube, the illumination pattern being visible from outside the gas tube.

The illumination pattern is characterized by at least one illumination parameter, derived by the control unit, such that the illumination pattern is indicative of the determined breath-related/physiological parameter and/or one or more of the assessed respiratory/physiological conditions.

According to some embodiments of the capnograph, the illumination module is configured to project a light beam into the gas tube, such that the light beam travels along a length of the gas tube, thereby producing the illumination pattern.

According to some embodiments of the capnograph, the illumination parameters include one or more of an intensity, a wavelength, a waveband/wavebands, a pulse-frequency, and a pulse-pattern.

According to some embodiments of the capnograph, the intensity of the light beam decreases by no more than 95%, 90%, 75%, or 50% in travelling from a first end of the gas tube to a second end thereof.

According to some embodiments of the capnograph, the illumination module includes a plurality of illumination sources configured to emit light at two or more different wavelengths separately or simultaneously.

According to some embodiments of the capnograph, the illumination source is a light emitting diode (LED), an LED array, a laser diode, or a laser diode array.

According to some embodiments of the capnograph, the LED array/laser diode array is a circular LED array.

According to some embodiments of the capnograph, the external agent is a processing module associated with at least one medical device.

According to some embodiments of the capnograph, the LED array/laser diode array is configured to emit light at two or more different wavelengths separately or simultaneously.

According to some embodiments of the capnograph, the capnograph further includes a housing. The housing includes the $CO_2$ sensing arrangement, the control unit, and the illumination module.

According to some embodiments of the capnograph, the intensity of the illumination pattern changes as a function of time, and a rate of change of the intensity is dependent on the obtained $CO_2$ sensing data.

According to some embodiments of the capnograph, the intensity of the illumination pattern changes synchronously with a respiration rate of the subject.

According to some embodiments of the capnograph, the illumination pattern is indicative of incorrect placement of the facially-fitting device.

According to some embodiments of the capnograph, the at least one breath-related/physiological parameter of the subject is selected from the group consisting of respiration rate, oxygen consumption, oxygen saturation, $SpO_2$, $CO_2$ concentration, $CO_2$ waveform, end-tidal $CO_2$ ($EtCO_2$), changes in $EtCO_2$, a slope of an increase in $CO_2$ concentration, a change in a slope of the increase in $CO_2$ concentration, time to rise to a predetermined percentage of a maximum value of $CO_2$ concentration, a change in time to rise to a predetermined percentage of a maximum value of $CO_2$ concentration, an angle of rise to a predetermined percentage of a maximum value of $CO_2$ concentration, a change in an angle of rise to a predetermined percentage of a maximum value of $CO_2$ concentration, breath-to-breath correlation, a change in breath-to-breath correlation, a $CO_2$ duty cycle, a change in $CO_2$ duty cycle, integrated pulmonary index (IPI), forced expiratory volume over a time interval, forced vital capacity, heart rate, blood pressure, body temperature, electrocardiogram (ECG), encephalogram (EEG), spirometry and/or any combination thereof.

According to some embodiments of the capnograph, the one or more respiratory/physiological conditions are selected from the group consisting of bronchitis, emphysema, asthma, upper or lower airway obstruction, a presence of bronchospasm, fever, anesthesia, hypothermia, bacterial infection(s) (for example, as detected along the gas tube), and/or any combination thereof.

According to an aspect of some embodiments, there is provide an illuminating connector, to be used with a capnograph. The connector includes:

A hollow body including a first end configured to be connected to a $CO_2$ gas port of a capnograph, and a second end fluidly connected to the first end and configured to be connected to a gas tube.

Control circuitry configured to determine one or more illumination parameters based at least on $CO_2$ sensing data obtained by the capnograph, such that the illumination pattern is indicative of one or more breath-related parameters and/or respiratory/physiological conditions of the subject.

At least one illumination source functionally associated with the control circuitry and configured to produce an illumination pattern in the gas tube when the first end is connected to the $CO_2$ gas port and the second end is connected to the gas tube. The illumination pattern is characterized by the illumination parameters.

According to some embodiments of the connector, the connector further includes a wireless communication unit. The wireless communication unit is configured to be wirelessly communicatively associated with a control unit of the capnograph and to receive from the control unit $CO_2$ sensing data and/or at least one breath-related/physiological parameter, determined by the control unit (and optionally, in addition, by some device other than the capnograph, e.g. a pulse oximeter), and/or one or more respiratory/physiological conditions assessed by the control unit (and optionally, in addition, by some device other than the capnograph, e.g. an electrocardiograph), and wherein, based thereon, the control circuitry is configured to determine the one or more illumination parameters.

According to some embodiments of the connector, the illumination source(s) is configured to project a light beam into the gas tube, such that the light beam travels along a length of the gas tube, thereby producing the illumination pattern.

According to some embodiments of the connector, the illumination parameters include one or more of an intensity, a wavelength, a waveband/wavebands, a pulse-frequency, and a pulse-pattern.

According to some embodiments of the connector, the intensity of the light beam decreases by no more than 95%, 90%, 75%, or 50% in travelling from a first end of the gas tube to a second end thereof.

According to some embodiments of the connector, the illumination sources are configured to emit light at two or more different wavelengths separately or simultaneously.

According to some embodiments of the connector, the illumination source(s) is an LED, an LED array, a laser diode, or a laser diode array.

According to some embodiments of the connector, the LED array/laser diode array is a circular LED array.

According to some embodiments of the connector, the LED array/laser diode array is configured to emit light at two or more different wavelengths separately or simultaneously.

According to some embodiments of the connector, the intensity of the illumination pattern changes as a function of time, and a rate of change of the intensity is dependent on the obtained $CO_2$ sensing data.

According to some embodiments of the connector, the intensity of the illumination pattern changes synchronously with a respiration rate of the subject.

According to some embodiments of the connector, the illumination pattern is indicative of incorrect placement of the facially-fitting device.

According to some embodiments of the connector, the at least one breath-related/physiological parameter of the subject is selected from the group consisting of respiration rate, oxygen consumption, oxygen saturation, $SpO_2$, $CO_2$ concentration, $CO_2$ waveform, $EtCO_2$, changes in $EtCO_2$, a slope of an increase in $CO_2$ concentration, a change in a slope of the increase in $CO_2$ concentration, time to rise to a predetermined percentage of a maximum value of $CO_2$ concentration, a change in time to rise to a predetermined percentage of a maximum value of $CO_2$ concentration, an angle of rise to a predetermined percentage of a maximum value of $CO_2$ concentration, a change in an angle of rise to a predetermined percentage of a maximum value of $CO_2$ concentration, breath-to-breath correlation, a change in breath-to-breath correlation, a $CO_2$ duty cycle, a change in $CO_2$ duty cycle, IPI, forced expiratory volume over a time interval, forced vital capacity, heart rate, blood pressure, body temperature, ECG, EEG, spirometry and/or any combination thereof.

According to some embodiments of the connector, the one or more respiratory/physiological conditions are selected from the group consisting of bronchitis, emphysema, asthma, upper or lower airway obstruction, a presence of bronchospasm, fever, anesthesia, hypothermia, bacterial infection(s), and/or any combination thereof.

According to an aspect of some embodiments, there is provided a disposable breath sampling assembly, configured for use with a capnograph. The breath sampling assembly includes:

A facially-fitting member configured to be fitted on a nasal/mouth region of a subject.

At least one gas tube fluidly connected, on a first end thereof, to the facially-fitting member, and configured to be detachably connectable on a second end thereof to a gas port of a capnograph.

Control circuitry configured to determine one or more illumination parameters based at least on $CO_2$ sensing data obtained by the capnograph, such that the illumination pattern is indicative of one or more breath-related/physiological parameters and/or respiratory/physiological conditions of the subject.

At least one illumination source functionally associated with the control circuitry and configured to produce an illumination pattern in the gas tube when the second end is connected to the gas tube. The illumination pattern is characterized by the illumination parameters.

The at least one illumination source is located in/on the gas tube or in the facially-fitting member such as to illuminate the gas tube.

According to some embodiments of the breath sampling assembly, the breath sampling assembly further includes a wireless communication unit. The wireless communication unit is configured to be wirelessly communicatively associated with a control unit of the capnograph and to receive from the control unit $CO_2$ sensing data and/or at least one breath-related/physiological parameter, determined by the control unit (and optionally, in addition, by some device other than the capnograph, e.g. a pulse oximeter), and/or one or more respiratory/physiological conditions assessed by the control unit (and optionally, in addition, by some device other than the capnograph, e.g. an electrocardiograph), and based thereon, the control circuitry is configured to determine the one or more illumination parameters.

According to some embodiments of the breath sampling assembly, the breath sampling assembly is a nasal cannula or oral/nasal cannula, and the facially-fitting member includes at least one nasal prong.

According to some embodiments of the breath sampling assembly, the gas tube includes at least one optical fiber. The at least one illumination source is configured to project light into the at least one optical fiber and thereby produce the illumination pattern.

According to some embodiments of the breath sampling assembly, the illumination source(s) is configured to project a light beam(s) into/in the gas tube, such that the light beam(s) travels along a length of the gas tube, thereby producing the illumination pattern.

According to some embodiments of the breath sampling assembly, the illumination parameters include one or more of an intensity, a wavelength, a waveband/wavebands, a pulse-frequency, and a pulse-pattern.

According to some embodiments of the breath sampling assembly, the intensity of the light beam decreases by no more than 95%, 90%, 75%, or 50% in travelling from a first end of the gas tube to a second end thereof.

According to some embodiments of the breath sampling assembly, the illumination sources are configured to emit light at two or more different wavelengths separately or simultaneously.

According to some embodiments of the breath sampling assembly, the illumination source(s) is an LED, an LED array, a laser diode, or a laser diode array.

According to some embodiments of the breath sampling assembly, the LED array/laser diode array is a circular LED array.

According to some embodiments of the breath sampling assembly, the LED array/laser diode array is configured to emit light at two or more different wavelengths separately or simultaneously.

According to some embodiments of the breath sampling assembly, the intensity of the illumination pattern changes as a function of time, and a rate of change of the intensity is dependent on the obtained $CO_2$ sensing data.

According to some embodiments of the breath sampling assembly, the intensity of the illumination pattern changes synchronously with a respiration rate of the subject.

According to some embodiments of the breath sampling assembly, the illumination pattern is indicative of incorrect placement of the facially-fitting device.

According to some embodiments of the breath sampling assembly, the at least one breath-related/physiological parameter of the subject is selected from the group consisting of respiration rate, oxygen consumption, oxygen saturation, $SpO_2$, $CO_2$ concentration, $CO_2$ waveform, $EtCO_2$, changes in $EtCO_2$, a slope of an increase in $CO_2$ concentration, a change in a slope of the increase in $CO_2$ concentration, time to rise to a predetermined percentage of a maximum value of $CO_2$ concentration, a change in time to rise to a predetermined percentage of a maximum value of $CO_2$ concentration, an angle of rise to a predetermined percentage of a maximum value of $CO_2$ concentration, a change in an angle of rise to a predetermined percentage of a maximum value of $CO_2$ concentration, breath-to-breath correlation, a change in breath-to-breath correlation, a $CO_2$ duty cycle, a change in $CO_2$ duty cycle, IPI, forced expiratory volume over a time interval, forced vital capacity, heart rate, blood pressure, body temperature, ECG, EEG, spirometry and/or any combination thereof.

According to some embodiments of the breath sampling assembly, the one or more respiratory/physiological conditions are selected from the group consisting of bronchitis, emphysema, asthma, upper or lower airway obstruction, a presence of bronchospasm, fever, anesthesia, hypothermia, bacterial infection(s), and/or any combination thereof.

According to an aspect of some embodiments, there is provided a method for providing a visual indication of at least one of breath-related/physiological parameters and/or respiratory/physiological conditions of a subject being monitored by a capnography system. The method includes:

Using a capnography system to obtain $CO_2$ sensing data of a subject.

Based at least on the $CO_2$ sensing data, deriving at least one illumination parameter.

Illuminating a gas tube, according to the at least one illumination parameter, such as to produce a visible illumination pattern in the gas tube.

The exhaled breath of the subject is conveyed via the gas tube from a facially-fitting member to the capnography system. The illumination pattern is indicative of at least one breath-related parameter and/or respiratory/physiological condition of the subject.

According to some embodiments of the method, in the step of illuminating, a light beam is projected into the gas tube, such that the light beam travels along a length of the gas tube, thereby producing the illumination pattern.

According to some embodiments of the method, the at least one illumination parameter includes one or more of an intensity, a wavelength, a waveband/wavebands, a pulse-frequency, and a pulse-pattern.

According to some embodiments of the method, the intensity of the light beam decreases by no more than 95%, 90%, 75%, or 50% in travelling from a first end of the gas tube to a second end thereof.

According to some embodiments of the method, a plurality of illumination sources, configured to emit light at two or more different wavelengths separately or simultaneously, are used to produce the illumination pattern.

According to some embodiments of the method, an LED, an LED array, a laser diode, and/or a laser diode array are used to produce the illumination pattern.

According to some embodiments of the method, the LED array/laser diode array is a circular LED array.

According to some embodiments of the method, the LED array/laser diode array is configured to emit light at two or more different wavelengths separately or simultaneously.

According to some embodiments of the method, the intensity of the illumination pattern changes as a function of time, and a rate of change of the intensity is dependent on the obtained $CO_2$ sensing data.

According to some embodiments of the method, the intensity of the illumination pattern changes synchronously with a respiration rate of the subject.

According to some embodiments of the method, the illumination pattern is indicative of incorrect placement of the facially-fitting member.

According to some embodiments of the method, the at least one breath-related/physiological parameter of the subject is selected from the group consisting of respiration rate, oxygen consumption, oxygen saturation, $SpO_2$, $CO_2$ concentration, $CO_2$ waveform, $EtCO_2$, changes in $EtCO_2$, a slope of an increase in $CO_2$ concentration, a change in a slope of the increase in $CO_2$ concentration, time to rise to a predetermined percentage of a maximum value of $CO_2$ concentration, a change in time to rise to a predetermined percentage of a maximum value of $CO_2$ concentration, an angle of rise to a predetermined percentage of a maximum value of $CO_2$ concentration, a change in an angle of rise to a predetermined percentage of a maximum value of $CO_2$ concentration, breath-to-breath correlation, a change in breath-to-breath correlation, a $CO_2$ duty cycle, a change in $CO_2$ duty cycle, IPI, forced expiratory volume over a time interval, forced vital capacity, heart rate, blood pressure, body temperature, ECG, EEG, spirometry and/or any combination thereof.

According to some embodiments of the method, the one or more respiratory/physiological conditions are selected from the group consisting of bronchitis, emphysema, asthma, upper or lower airway obstruction, a presence of bronchospasm, fever, anesthesia, hypothermia, bacterial infection(s), and/or any combination thereof.

According to an aspect of some embodiments, there is provided a computer-readable storage medium including software executable by a processor(s). The software is configured to, based at least on $CO_2$ sensing data obtainable from a capnograph, derive illumination instructions for producing an illumination pattern in a breath-sampling tube. The illumination pattern is indicative of at least one breath-related/physiological parameters and/or respiratory/physiological conditions of a subject.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

BRIEF DESCRIPTION OF THE FIGURES

Some embodiments of the disclosure are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the disclosure. For the sake of clarity, some objects depicted in the figures are not to scale.

In the Figures.

DETAILED DESCRIPTION

The principles, uses, and implementations of the teachings herein may be better understood with reference to the accompanying description and figures. Upon perusal of the description and figures present herein, one skilled in the art will be able to implement the teachings herein without undue effort or experimentation. In the figures, same reference numerals refer to same parts throughout.

In the description and claims of the application, the words "include" and "have", and forms thereof, are not limited to members in a list with which the words may be associated.

As used herein, the term "about" may be used to specify a value of a quantity or parameter (e.g. the length of an element) to within a continuous range of values in the neighborhood of (and including) a given (stated) value. According to some embodiments, "about" may specify the value of a parameter to be between 80% and 120% of the given value. For example, the statement "the length of the element is equal to about 1 m" is equivalent to the statement "the length of the element is between 0.8 m and 1.2 m". According to some embodiments, "about" may specify the value of a parameter to be between 90% and 110% of the given value. According to some embodiments, "about" may specify the value of a parameter to be between 95% and 105% of the given value.

Figure 1:
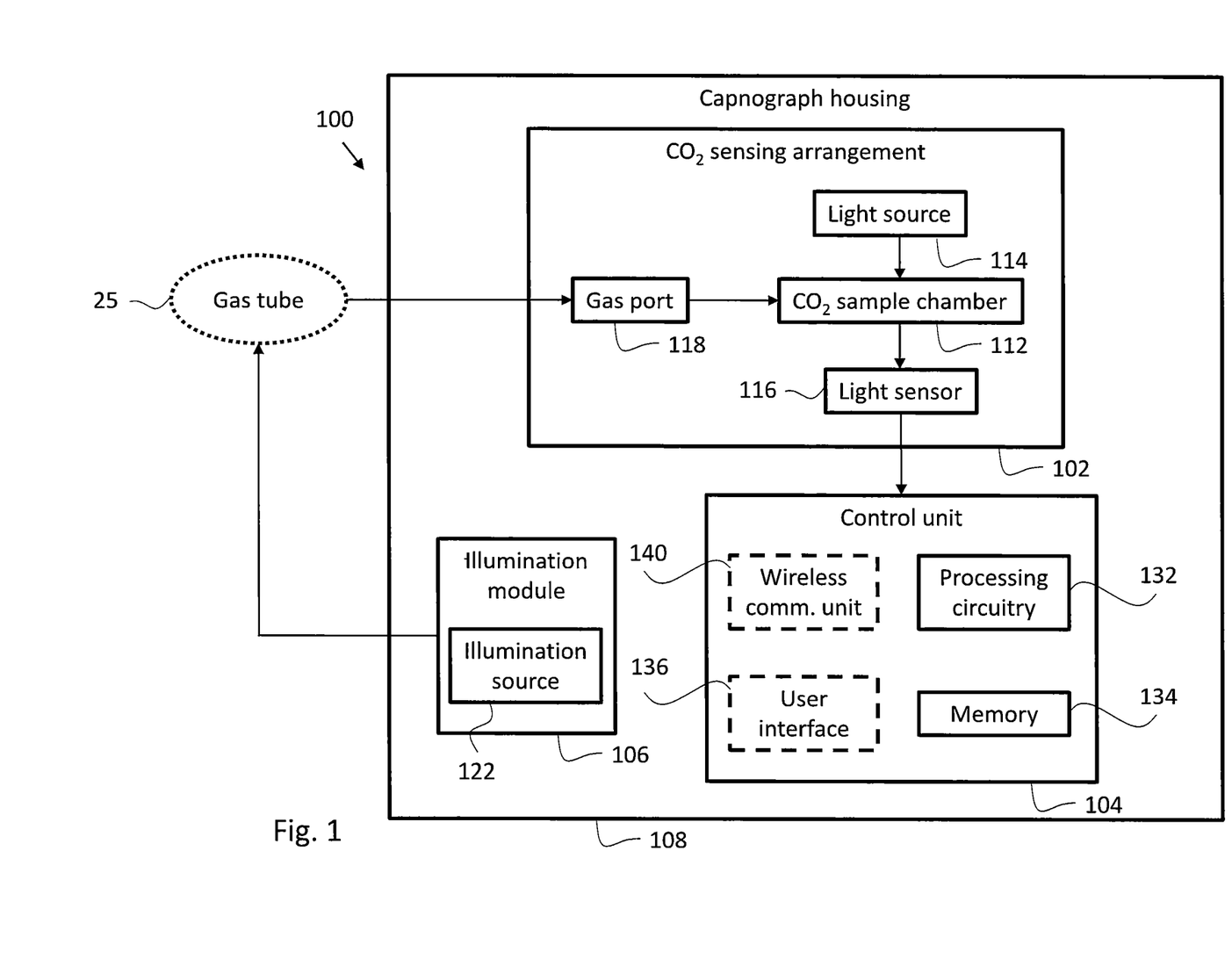
FIG. 1 is a block diagram of a capnograph including an illumination module, according to some embodiments.

FIG. 1 is a block diagram of a capnograph 100, according to some embodiments. Capnograph 100 is configured to be used in conjunction with a facially-fitting device 15 (shown in FIG. 2a) to measure $CO_2$ levels (e.g. concentration or partial pressure) in exhaled breath of a monitored subject, as elaborated on below. Facially-fitting device 15 is configured to collect the exhaled breath of the subject and to deliver the exhaled breath to capnograph 100, as known in the art of capnography and as elaborated on below.

Capnograph 100 includes a $CO_2$ sensing arrangement 102, a control unit 104, an illumination module 106, and a capnograph housing (casing) 108. Capnograph housing 108 includes $CO_2$ sensing arrangement 102, control unit 104, and illumination module 106.

According to some embodiments, $CO_2$ sensing arrangement 102 includes a $CO_2$ sample chamber 112, a light source 114, a light sensor 116, and a gas port 118. Gas port 118 is fluidly coupled, on an inner end thereof (within capnograph housing 108; not shown in the figures), to $CO_2$ sample chamber 112. Gas port 118 is configured to be fluidly coupled, on an outer end thereof (exposed on capnograph housing 108; not shown in the figures), to a gas tube 25 of facially-fitting device 15, such as to allow delivery of exhaled breath of a subject to $CO_2$ sample chamber 112. (In FIG. 1, gas tube 25 is represented by an (dotted) oval box, instead of a rectangular box, to indicate that gas tube 25 is not a part of capnograph 100.)

$CO_2$ sensing arrangement 102 may further include a pump (not shown) to facilitate delivery of exhaled breath into $CO_2$ sample chamber 112. Light source 114 is configured to project light into $CO_2$ sample chamber 112, such as to pass through gas in $CO_2$ sample chamber 112 and to be incident on light sensor 116, as known in the art of capnography. According to some embodiments, light source 114 is an infrared (IR) light source, and light sensor 116 is an IR light sensor configured to measure intensity of IR light incident thereon. $CO_2$ sensing arrangement 102 may further include optical elements (not shown), such as an optical filter (e.g. an IR filter configured to "screen out" non-IR light).

$CO_2$ sensing arrangement 102 is configured to obtain $CO_2$ sensing data from the exhaled breath of the subject, wherefrom $CO_2$ levels in the exhaled breath of the subject may be obtained, as known in the art of capnography.

Illumination module 106 is positioned in, or near, gas port 118 and includes an illumination source(s) 122 (e.g. one or more light bulbs). Illumination module 106 is configured to be associated to gas tube 25, such as to allow producing an illumination pattern within gas tube 25, which is visible from the outside of gas tube 25 (e.g. gas tube 25 is transparent or semi-transparent), as elaborated on below and in the description of FIGS. 2a-2d. The illumination pattern is determined (characterized) by one or more illumination parameters, which are in turn determined by control unit 104 based on $CO_2$ sensing data of a subject monitored by capnograph 100. The illumination pattern is configured to provide a visual indication, e.g. to medical personnel, of a respiratory status (e.g. respiratory patterns) of the subject, of a determined level(s) of a breath-related/physiological parameter(s) of the subject, and/or of one or more physiological conditions (beyond the respiratory status, such as, for example, fever and hypothermia) of the subject, as elaborated on below.

According to some embodiments, illumination source 122 is configured to project a light beam into gas tube 25, thereby producing the illumination pattern. According to some embodiments, illumination source 122 is a light-emitting diode (LED) or a laser-diode. According to some embodiments, illumination module 106 may include optical elements, such as one or more lenses and/or reflectors (e.g. parabolic reflectors), configured to focus light emitted by illumination source 122. According to some embodiments, the light beam may be made to flicker at a controlled rate/pattern.

Figures 2A, 2B, 2C:
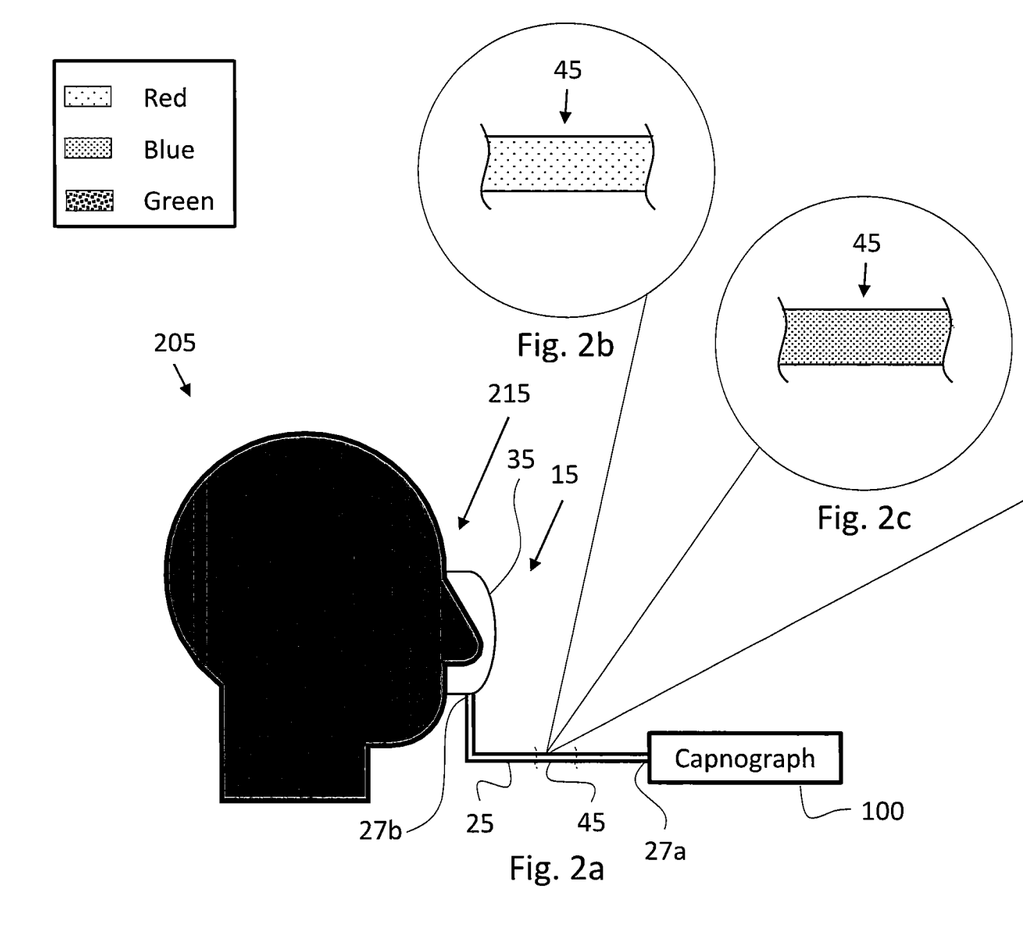
FIG. 2a schematically depicts the capnograph of FIG. 1 used in conjunction with a facially-fitting device to monitor a subject, according to some embodiments.
FIG. 2b schematically depicts a portion of a gas tube of the facially-fitting device of FIG. 2a illuminated in red by the illumination module of the capnograph, according to some embodiments.
FIG. 2c schematically depicts a portion of a gas tube of the facially-fitting device of FIG. 2a illuminated in blue by the illumination module of the capnograph, according to some embodiments.

Illumination module 106 is configured such that at least some light rays (in a light beam projected into gas tube 25) are transmitted to the outside of gas tube 25 via inner walls of gas tube 25, thereby rendering the illumination pattern visible from the outside of gas tube 25. That is, at least some of the light rays do not undergo total internal reflection off the inner walls of gas tube 25. (In other words, gas tube 25 essentially functions as a "leaking" waveguide.) According to some embodiments, the intensity of a light beam (produced by illumination source 122) may decrease by no more than about 95% in travelling through gas tube 25 from a first tube end 27a of gas tube 25 (connected to gas port 118) to a second tube end 27b of gas tube 25 (connected to a cup member of facially-fitting device 15, as shown in FIG. 2a). According to some embodiments, the intensity of the light beam may decrease by no more than about 90%, 75%, or even 50% in travelling through gas tube 25.

According to some embodiments, illumination source 122 is configured to produce light beams of different colors (e.g. red and blue) separately (one color at a time) and optionally simultaneously. According to some such embodiments, illumination source 122 includes at least two LEDs, e.g. a red LED and a blue LED. According to some such embodiments, illumination source 122 includes at least two laser diodes. According to some embodiments, illumination source 122 is an LED array/laser diode array, e.g. a circular LED array/laser diode array. According to some embodiments, the LEDs/laser diodes in the LED array/laser diode array are arranged in a closed loop on an inner wall of gas port 118, e.g. in a circle when the inner wall defines a cylinder. According to some embodiments, the LED array/laser diode array is configured to emit light at two or more different colors separately and, optionally, simultaneously.

According to some embodiments, control unit 104 includes processing circuitry 132, a memory 134, and optionally a user interface 136. (Optional components, such as user interface 136, are denoted by boxes with a dashed outline.) Control unit 104 is functionally associated with $CO_2$ sensing arrangement 102 and illumination module 106. Control unit 104 is configured to receive $CO_2$ sensing data from $CO_2$ sensing arrangement 102 and to determine, based on the $CO_2$ sensing data, $CO_2$ levels (e.g. concentration or partial pressure) in the exhaled breath of the subject. Control unit 104 may further be configured to determine, based on the $CO_2$ sensing data, other breath-related/physiological parameters, such as respiration rate, oxygen consumption, oxygen saturation, $SpO_2$, $CO_2$ concentration, $CO_2$ waveform, end-tidal $CO_2$ ($EtCO_2$), changes in $EtCO_2$, a slope of an increase in $CO_2$ concentration, a change in a slope of the increase in $CO_2$ concentration, time to rise to a predetermined percentage of a maximum value of $CO_2$ concentration, a change in time to rise to a predetermined percentage of a maximum value of $CO_2$ concentration, an angle of rise to a predetermined percentage of a maximum value of $CO_2$ concentration, a change in an angle of rise to a predetermined percentage of a maximum value of $CO_2$ concentration, and base pulmonary function measures, e.g. the forced expiratory volume over 1 second (FEV1; provides a measure of flow), the forced vital capacity (FVC; provides a measure of volume), and the ratio FEV1/FVC. Optionally, control unit 104 may further be configured to assess respiratory condition(s) such as a presence of bronchospasm, a severity of the bronchospasm, bronchitis, emphysema, asthma, and upper or lower airway obstruction or other respiratory deficiencies, and/or to assess physiological condition(s) (beyond respiratory status) such as degree of anesthesia or pain. Control unit 104 is further configured, based on the determined breath-related parameter(s) of the subject, and/or the assessed respiratory/physiological condition(s) thereof, to instruct illumination module 106 to produce an illumination pattern in gas tube 25 which is indicative of the determined breath-related/physiological parameter(s) and/or the assessed respiratory/physiological condition(s), as elaborated on below in the description of FIGS. 2a-2d.

User interface 136 may include a monitor (not shown) configured to display a capnogram of the subject. According to some embodiments, user interface 136 include knobs/buttons (not shown) configured to allow a user (e.g. medical personnel) to e.g. switch on/off capnograph 100 and optionally control other operable features of capnograph 100, such as data to be analyzed/displayed. According to some embodiments, the monitor is a touch screen.

Optionally, control unit 104 may include a wireless communication unit 140 (e.g. a Wi-Fi transmitter or transceiver) allowing wireless transmission of obtained data (e.g. breath-related parameters) to a remote agent, such as a hospital computer, a physician's computer, or a computer at a nurses' station.

Processing circuitry 132 may be an application specific integrated circuitry (ASIC), a programmable processing circuitry such as an FPGA, firmware, and/or the like, and is configured to process the $CO_2$ sensing data, obtained by $CO_2$ sensing arrangement 102, to determine the breath-related/physiological parameter(s) (and optionally to assess a respiratory/physiological condition(s) of the subject), and, based thereon, to determine the illumination parameter(s). According to some embodiments, memory 134 is a non-transitory memory, including software, executable by processing circuitry 132, configured for computing the breath-related/physiological parameter(s) and illumination parameter(s), and optionally assessing respiratory/physiological conditions of the subject. Memory 134 may include a solid-state memory, a magnetic memory, a photonic memory, and/or the like. According to some embodiments, the memory includes both non-transitory memory components and transitory memory components.

Figure 2D:
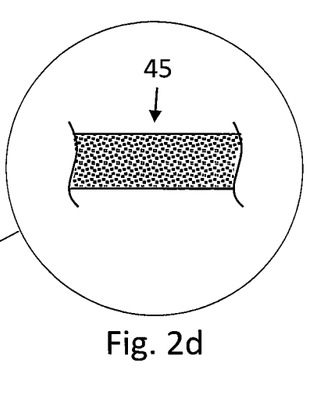
FIG. 2d schematically depicts a portion of a gas tube of the facially-fitting device of FIG. 2a illuminated in green by the illumination module of the capnograph, according to some embodiments.

Elements (such as batteries or a connection to an external power source) for powering capnograph 100 elements (e.g. illumination source 122, processing circuitry 132) are not shown in FIGS. 1-2d. Electrical wires functionally associating capnograph 100 elements (e.g. illumination module 106 to control unit 104, processing circuitry 132 to memory 134) are also not shown.

According to some embodiments, the illumination parameter(s) may be determined by control unit 104 based also on additional sensing data which was not obtained by capnograph 100 but by some other medical sensing device, such as a pulse oximeter or an electrocardiograph. Thus, for example, the illumination pattern may be determined based on $CO_2$ sensing data (obtained by capnograph 100) and an electrocardiogram (ECG) obtained by an electrocardiograph. According to some such embodiments, capnograph 100 may be directly communicatively associated with the medical sensing device(s) used to obtain the additional sensing data (e.g. by Wi-Fi), or indirectly communicatively associated therewith via an external agent such as a hospital computer. According to some such embodiments, the additional sensing data may be fed into capnograph 100 by medical personnel, e.g. via user interface 136.

FIG. 2a schematically depicts a subject 205 monitored by capnograph 100. Subject 205 is shown wearing facially-fitting device 15 over a face 215 of subject 205. According to some embodiments, and as depicted in FIG. 2a, facially-fitting device 15 is in the form of a mask, including a cup member 35 configured to be fitted over a mouth-nose region (not numbered) of face 215. According to some embodiments, not depicted in FIG. 2a, facially-fitting device 15 is in the form of a nasal cannula, as known in the art of capnography. Gas tube 25 is connected, on first tube end 27a, to gas port 118, and, on second tube end 27b, to cup member 35. In operation, breath exhaled by subject 205 is conveyed via gas tube 25 and gas port 118 into $CO_2$ sample chamber 112.

FIG. 2b provides a schematic close-up view of a tube portion 45 of gas tube 25 when capnograph 100 is used in conjunction with facially-fitting device 15, as depicted in FIG. 2a. Gas tube 25 is shown illuminated in red due to passage therethrough of a red light beam projected (into gas tube 25) by illumination module 106. The red light beam constitutes the illumination pattern. According to some embodiments, the red illumination pattern may, as a non-limiting example, indicate severe bronchospasm. According to some embodiments, the red illumination pattern may, as a non-limiting, example, indicate low $EtCO_2$ levels. FIG. 2c provides a schematic close-up view of tube portion 45 of gas tube 25 when capnograph 100 is used in conjunction with facially-fitting device 15, as depicted in FIG. 2a. Gas tube 25 is shown illuminated in blue due to passage therethrough of a blue light beam projected (into gas tube 25) by illumination module 106. The blue light beam constitutes the illumination pattern. According to some embodiments, the blue illumination pattern may, as a non-limiting example, indicate mild bronchospasm.

According to some embodiments, wherein illumination module 106 is configured to produce illumination patterns at two or more different colors, at least two different assessed respiratory/physiological conditions can be indicated using the illumination patterns at essentially the same time. For example, illumination module 106 may indicate both pulmonary perfusion and alveolar ventilation by alternately producing the red illumination pattern and the blue illumination pattern one after the other. Or, for example, illumination module 106 may be configured to simultaneously project the red and blue light beams (into gas tube 25), thereby producing a purple illumination pattern, which may, for example, indicate potential presence of both pulmonary perfusion and alveolar ventilation. Similarly, determined levels of two or more different breath-related/physiological parameters can be indicated using two or more respective illumination patterns, e.g. in a sequence.

FIG. 2d provides a schematic close-up view of tube portion 45 of gas tube 25 when capnograph 100 is used in conjunction with facially-fitting device 15, as depicted in FIG. 2a. Gas tube 25 is shown illuminated in green due to passage therethrough of a green light beam projected (into gas tube 25) by illumination module 106. The green light beam constitutes the illumination pattern. According to some embodiments, the green illumination pattern may indicate, for example, normal/regular respiratory status.

According to some embodiments, an absence of an illumination pattern may indicate, for example, normal/regular respiratory status (that is, illumination patterns are used to indicate only irregular respiratory status and/or abnormal physiological conditions). Additionally or alternatively, absence of illumination may indicate that no sampling is being performed.

According to some embodiments, illumination source 122 may be configured to project a pulsed light beam into gas tube 25, thereby producing a flickering illumination pattern. For example, a flickering light pattern may indicate increased $CO_2$ concentration, while a constant illumination pattern may indicate reduced $CO_2$ concentration. According to some embodiments, the frequencies of the pulses may indicate different respiratory/physiological conditions, respectively. According to some embodiments, the frequencies of the pulses may indicate different levels of a breath-related/physiological parameter, respectively. According to some embodiments, illumination source 122 may be configured to project a light beam into gas tube 25 in bursts of pulses. In such embodiments, the pattern of pulses within a burst (e.g. the number of pulses within the burst, times intervals between consecutive pulses), as well as the rate of bursts may function to indicate different respiratory/physiological conditions or different levels of a breath-related/physiological parameter.

According to some embodiments, the illumination pattern may be synchronized with the respiration rate (respiratory rate) of the subject, e.g. the illumination pattern may flicker/glow according to the respiration rate of the subject.

According to some embodiments, control unit 104 is configured to allow a user of capnograph 100 (e.g. medical personnel) to select what type(s) of information is indicated by the illumination pattern. For example, the user may select between presenting correct/incorrect placement of facially-fitting device 15 and the respiration rate of subject 205. According to some embodiments, control unit 104 may be programmed to allow first one type of information to be conveyed and then another. For example, correct/incorrect placement of facially-fitting device 15 may first be indicated followed by the respiration rate of subject 205 (when correct placement has been determined).

It is noted that incorrect placement (fitting) of facially-fitting device 15 on face 215 may lead to significantly lower $CO_2$ levels recorded by $CO_2$ sensing arrangement 102. Thus, according to some embodiments, when the sensed $CO_2$ levels are below a threshold value, the illumination pattern signals possible incorrect placement of facially-fitting device 15, e.g. a red illumination pattern, or a rapidly flickering illumination pattern may indicate incorrect placement.

According to some embodiments, control unit 104 may be configured to determine the light pattern based on an integrated pulmonary index (IPI) score of the subject. According to some embodiments, a red (i.e. red-colored) illumination pattern may, as a non-limiting example, indicate a low IPI score, while a blue (i.e. blue-colored) illumination pattern, may indicate, as a non-limiting example, a high IPI score. According to some such embodiments, capnograph 100 may be configured to receive (e.g. by wire via a USB port (not shown) or wirelessly), pulse oximetry data to determine the IPI score. According to some embodiments, the IPI score may be determined on an external agent (e.g. an IPI module or a hospital computer), with the determined IPI score being sent to capnograph 100. In such embodiments, capnograph 100 may be configured to send the $CO_2$ sensing data to the external agent. According to some such embodiments, user interface 136 may be configured to allow a user (e.g. medical personnel) to input the pulse oximetry data.

Figure 3:
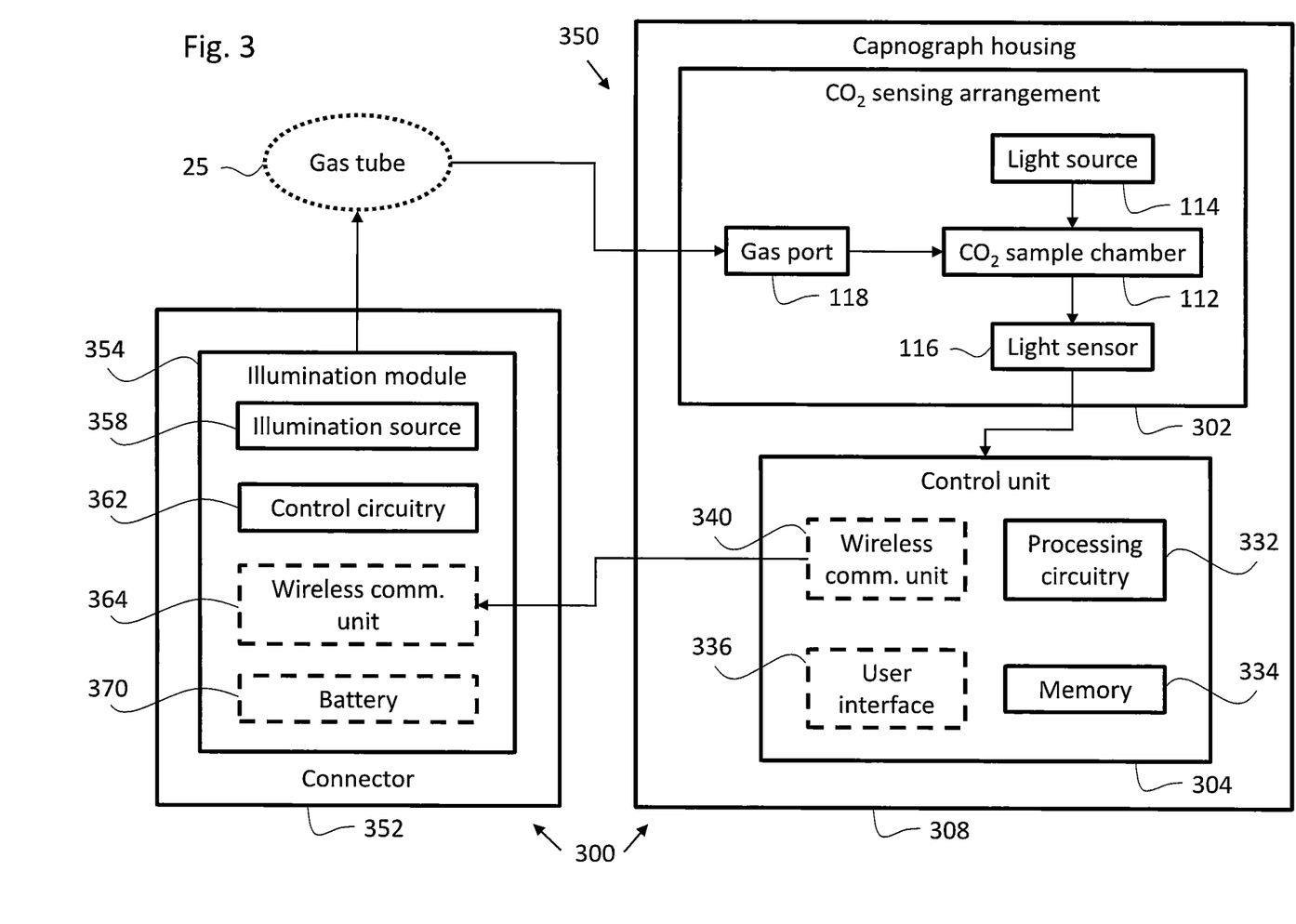
FIG. 3 is a block diagram of a capnography arrangement including an illuminating connector and a capnograph, the illuminating connector includes an illumination module and is configured to be connected on one end thereof to the capnograph and on the other end thereof to a facially-fitting device.

FIG. 3 depicts a capnograph arrangement 300. Capnograph arrangement 300 includes a capnograph 350 and an illuminating connector (illuminating connecting element) 352. Connector 352 can be connected (e.g. detachably connected) to capnograph 350, as elaborated on below. Capnograph 350 includes a $CO_2$ sensing arrangement 302 similar to $CO_2$ sensing arrangement 102, a control unit 304 similar to control unit 104, and a capnograph housing 308 which includes $CO_2$ sensing arrangement 302 and control unit 304. Control unit 304 includes processing circuitry 332, a memory 334, optionally a user interface 336, and optionally a wireless communication unit 340, similar to processing circuitry 132, memory 134, user interface 136, and wireless communication unit 140, respectively.

Connector 352 is hollow. According to some embodiments, connector 352 is cylindrical, being shaped as a short tube. Connector 352 is configured to be fluidly connected on a first end thereof to gas port 118 (and thereby to fluidly couple to $CO_2$ sample chamber 112), and on a second end thereof to a gas tube of a facially-fitting device, such as gas tube 25 of facially-fitting device 15. The first end of connector 352 may be shaped similarly to first tube end 27a to facilitate connection of the first end of connector 352 to gas port 118. Similarly, the second end of connector 352 may be shaped similarly to the outer end of gas port 118 to facilitate connection of the second end of connector 352 to first tube end 27a.

Connector 352 includes an illumination module 354. As used herein, connector 352 may be said to be "installed" when gas tube 25 is fluidly coupled to capnograph 350 via connector 352 (i.e. when the first and second ends of connector 352 are connected to gas port 118 and first tube end 27a, respectively). As elaborated on below, illumination module 354 is configured to allow production of an illumination pattern within gas tube 25 when connector 352 is installed.

Illumination module 354 includes an illumination source(s) (e.g. one or more light bulbs) 358, control circuitry 362 (e.g. processing circuitry and a memory, a microcontroller), and optionally a wireless communication unit 364 (e.g. a Wi-Fi or Bluetooth receiver or transceiver). Illumination source 358 is functionally associated with control circuitry 362. Wireless communication unit 364 is communicatively associated with control circuitry 362. According to some embodiments, illumination module 354 further includes a battery 370 powering illumination source 358, control circuitry 362, and wireless communication unit 364. Electrical wires functionally associating illumination module 354 elements are not shown.

According to some embodiments, connector 352 may be communicatively associated with capnograph 350 by wire (e.g. via a USB port (not shown) in capnograph 350).

According to some embodiments, control circuitry 362 may be configured to receive from control unit 304 one or more breath-related/physiological parameters (relayed via wireless communication units 340 and 364), determined by control unit 304 based on the $CO_2$ sensing data of the subject. Additionally/alternatively, control circuitry 362 may be configured to receive from control unit 304 data specifying one or more respiratory/physiological conditions assessed by control unit 304 based on the $CO_2$ sensing data. Based on the information, received from control unit 304, control circuitry 362 determines one or more illumination parameters specifying an illumination pattern (such as the illumination patterns described in the description of capnograph 100), which is indicative of the breath-related/physiological parameter(s) and/or respiratory/physiological condition(s). Control circuitry 362 is configured to instruct illumination source 358 to produce the determined illumination pattern.

According to some embodiments, control circuitry 362 may receive from control unit 304 the $CO_2$ sensing data. In such embodiments, control circuitry 362 may be configured to determine the illumination pattern directly from the $CO_2$ sensing data.

According to some embodiments, the illumination parameter(s) may be determined by control unit 304/control circuitry 362 based also on additional sensing data which was not obtained by capnograph 350 but by some other medical sensing device, essentially as described in the description of capnograph 100.

According to some embodiments, control circuitry 362 is configured to allow a user of capnograph arrangement 300 to select what type(s) of information is indicated by the illumination pattern. In such embodiments, capnograph arrangement 300 may include an external controller (e.g. a remote control (not shown) operated by the user) configured to command control circuitry 362 (and wirelessly associated therewith).

Illumination source 358 may be attached to/positioned on an inner surface (not shown) of connector 352, e.g. in a circular arrangement when the inner surface defines a cylinder. According to some embodiments, illumination source 358 is an LED/laser diode or a LED/laser diode array.

According to some embodiments, connector 352 is configured to be used with commercially available capnographs including a wireless communication unit, such as wireless communication unit 340, which is configured to allow sending analyzed data (e.g. determined breath-related/physiological parameters and/or assessed respiratory/physiological conditions) to one or more external agents, and, as such, may also allow communicatively associating the capnograph with connector 352.

According to some embodiments, connector 352 may similarly be used with capnographs which include distinct components that are not housed within a common housing. Specifically, according to some embodiments, connector 352 may be similarly used with capnographs wherein the sensing arrangement and the control unit (analyzing unit or controller) are distinct components (not housed within a common housing), which may communicate wirelessly. To be used with such capnographs, connector 352 may be plugged into the gas port of the sensing arrangement, and wireless communication may be established between connector 352 and the control unit.

According to some embodiments, the assessed respiratory/physiological conditions are derived from the shape of the capnogram.

As used herein, according to some embodiments, the term "illumination pattern" with reference to an illumination of a gas tube (such as the illumination of gas tube 25 by illumination module 106 or 354) may refer to a temporal pattern (e.g. a flickering light beam), as well as to a spatial pattern (e.g. wherein an interference pattern is formed within or on the gas tube).

As used herein, according to some embodiments, the term "capnography system" may refer to a capnograph/capnograph arrangement (such as capnograph 100/capnograph arrangement 300) together with a facially-fitting device, such as facially-fitting device 15.

According to an aspect of some embodiments, there is provided a disposable breath-sampling assembly, such as a nasal cannula. The breath-sampling assembly includes a gas tube which may be integrally formed as part of the breath-sampling assembly or may be connectable to a facially-fitting member of the breath-sampling assembly (e.g. to a main body portion of the nasal cannula which includes/is connected to the nasal prongs) on a first end of the gas tube. The gas tube is configured to be connected on a second end thereof to a capnograph gas port, such as gas port 118.

According to some embodiments, the gas tube includes internal components similar to connector 352 (i.e. an illumination source, control circuitry, and a wireless communication unit similar to illumination source(s) 358, control circuitry 362, and wireless communication unit 364, respectively), being thereby configured to be illuminated when used in conjunction with a capnograph, such as capnograph 350.

According to some embodiments, the internal components are housed at/near the first end of the gas tube and the illumination source is configured to project a light beam toward the second end of the gas tube, and thereby form an illumination pattern. According to some embodiments, the internal components are housed at/near the second end of the gas tube and the illumination source is configured to project a light beam toward the first end of the gas tube and thereby form an illumination pattern. According to some embodiments, the internal components are housed at/near a central segment of the gas tube and the illumination source is configured to project light beams both toward the first end and the second end of the gas tube and thereby form an illumination pattern.

According to some embodiments, the gas tube includes one or more optical fibers, which extend along the length thereof. The illumination source(s) is configured to project light into the optical fibers and thereby to form the illumination pattern. According to some embodiments, wherein the gas tube includes a plurality of optical fibers, different optical fibers may be illuminated in different colors, such that each of the optical fibers corresponds to a different parameter. It is noted, that the illumination patterns formed in the optical fibers may be both temporal and spatial.

According to some embodiments, the facially-fitting member houses the internal components, such as to allow illuminating the gas tube via the first end thereof. According to some embodiments, some of the internal components are housed in the facially-fitting member (e.g. the control circuitry and the wireless communication unit) and some of the internal components are housed in the gas tube (e.g. the illumination source(s) may be housed at/near the first end of the gas tube). According to some embodiments, the illumination parameter(s) may be determined by the control unit of the capnograph (with which the breath-sampling assembly is used), and/or the control circuitry of the illumination module of the breath-sampling assembly, based also on additional sensing data which was not obtained by the capnograph, but by some other medical sensing device, essentially as described in the description of capnograph 100.

As used herein, according to some embodiments, the terms "illumination source(s)" and "indicator lights" with reference to a capnograph/capnograph arrangement/capnography system are used interchangeably.

The scope of the disclosure covers, according to some embodiments, any breath sampling devices/systems and/or related components/consumables involving a tube for conveying exhaled breath and not only capnographs/capnograph arrangements/capnography systems and related components/consumables.

As used herein, according to some embodiments, the terms "respiratory status" and "respiratory condition" are used interchangeably.

As used herein, according to some embodiments, the terms "disposable breath sampling assembly" (with reference to an illuminating breath sampling assembly as described above) and "illuminated consumables" are used interchangeably.

According to some embodiments, the terms "pulmonary index value" or "integrated pulmonary index value" may refer to a pulmonary index and/or a respiratory index. The terms "pulmonary index value" or "integrated pulmonary index value" may further relate to a respiratory and cardiac index and/or to a pulmonary and cardiac index.

According to some embodiments, the determined breath-related/physiological parameter(s) and/or the assessed respiratory/physiological condition(s), may additionally be partially determined/assessed by additional sensor(s)/medical device(s) (other than a capnograph-related sensor/capnograph) and, optionally, computational devices (e.g. a computer, a processing module) associated thereto. The additional sensor(s)/medical device(s) may be used to sense/measure/calculate/determine various health-related parameters. The additional sensor(s)/medical sensing device(s) may include, for example, an oximeter, spirometer, heart-rate sensor(s), blood pressure sensor(s), electrocardiograph (ECG); electroencephalograph (EEG), ultrasound device, IPI module, and the like, and/or any combination thereof.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. No feature described in the context of an embodiment is to be considered an essential feature of that embodiment, unless explicitly specified as such.

Although steps of methods according to some embodiments may be described in a specific sequence, methods of the disclosure may include some or all of the described steps carried out in a different order. A method of the disclosure may include a few of the steps described or all of the steps described. No particular step in a disclosed method is to be considered an essential step of that method, unless explicitly specified as such.

Although the disclosure is described in conjunction with specific embodiments thereof, it is evident that numerous alternatives, modifications and variations that are apparent to those skilled in the art may exist. Accordingly, the disclosure embraces all such alternatives, modifications and variations that fall within the scope of the appended claims. It is to be understood that the disclosure is not necessarily limited in its application to the details of construction and the arrangement of the components and/or methods set forth herein. Other embodiments may be practiced, and an embodiment may be carried out in various ways.

The phraseology and terminology employed herein are for descriptive purposes and should not be regarded as limiting. Citation or identification of any reference in this application shall not be construed as an admission that such reference is available as prior art to the disclosure. Section headings are used herein to ease understanding of the specification and should not be construed as necessarily limiting.

What is claimed is:

1. A capnograph for use in conjunction with a facially-fitting device for exhaled breath sampling, the capnograph comprising:

a $CO_2$ sensing arrangement configured to receive, via a gas tube fluidly connected to a facially-fitting device, exhaled breath from a subject monitored by the capnograph;

a control unit configured to process $CO_2$ sensing data, received from the $CO_2$ sensing arrangement to assess two or more respiratory/physiological conditions of the subject based at least on the $CO_2$ sensing data; and an illumination module comprising an illumination source and configured to be associated to the gas tube and to produce two distinct illumination patterns in the gas tube, the illumination patterns being visible from outside the gas tube;

wherein the illumination patterns comprise a first illumination pattern and a second illumination pattern characterized by at least two illumination parameters, derived by the control unit, such that the illumination patterns are indicative of the at least two assessed respiratory/physiological conditions, wherein the first illumination pattern comprises a first color indicative of a first condition and the second illumination pattern comprises a second, different color indicative of a second condition, and wherein the first and second patterns are produced at the same time or sequentially in the gas tube.

2. The capnograph of claim 1, wherein the illumination module is configured to project a light beam into the gas tube, and wherein the light beam travels along a length of the gas tube, thereby producing the illumination patterns.

3. The capnograph of claim 2, wherein at least one illumination parameters comprises one or more of an intensity, a wavelength, a waveband/wavebands, a pulse-frequency, and a pulse-pattern.

4. The capnograph of claim 3, wherein the intensity of the light beam decreases by no more than 95%, 90%, 75%, or 50% in travelling from a first end of the gas tube to a second end thereof.

5. The capnograph of claim 3, wherein the illumination module comprises a plurality of illumination sources configured to emit light at two or more different wavelengths separately or simultaneously.

6. The capnograph of claim 3, wherein the illumination source is a light emitting diode (LED), an LED array, a laser diode, or a laser diode array.

7. The capnograph of claim 6, wherein the LED array/laser diode array is configured to emit light at two or more different wavelengths separately or simultaneously.

8. The capnograph of claim 3, wherein the capnograph further comprises a housing, which housing comprises the $CO_2$ sensing arrangement, the control unit, and the illumination module.

9. The capnograph of claim 3, wherein the assessed respiratory/physiological conditions are determined from the group consisting of respiration rate, $CO_2$ concentration, $CO_2$ waveform, end-tidal $CO_2$ (EtCO$_2$), changes in EtCO$_2$, a slope of an increase in $CO_2$ concentration, a change in a slope of the increase in $CO_2$ concentration, time to rise to a predetermined percentage of a maximum value of $CO_2$ concentration, a change in time to rise to a predetermined percentage of a maximum value of $CO_2$ concentration, an angle of rise to a predetermined percentage of a maximum value of $CO_2$ concentration, a change in an angle of rise to a predetermined percentage of a maximum value of $CO_2$ concentration, breath-to-breath correlation, a change in breath-to-breath correlation, a $CO_2$ duty cycle, a change in $CO_2$ duty cycle, integrated pulmonary index (IPI), forced expiratory volume over a time interval, forced vital capacity and/or any combination thereof.

10. The capnograph of claim 3, wherein the respiratory/physiological conditions are selected from the group consisting of bronchitis, emphysema, asthma, upper or lower airway obstruction, a presence of bronchospasm, fever, anesthesia, hypothermia, bacterial infection, and/or any combination thereof.

11. The capnograph of claim 1, wherein the intensity of the illumination patterns change as a function of time, and wherein a rate of change of the intensity is dependent on the obtained $CO_2$ sensing data.

12. The capnograph of claim 11, wherein the intensity of the illumination patterns change synchronously with a respiration rate of the subject.

13. The capnograph of claim 1, wherein the illumination module is configured to produce a further illumination pattern in the gas tube indicative of incorrect placement of the facially-fitting device.

14. An illuminating connector, to be used with a capnograph, the connector comprising:
a hollow body comprising a first end configured to be connected to a $CO_2$ gas port of a capnograph, and a second end fluidly connected to the first end and configured to be connected to a gas tube;
control circuitry configured to determine one or more illumination parameters based at least on $CO_2$ sensing data obtained by the capnograph to produce a first illumination pattern and a second illumination pattern, wherein the first illumination pattern comprises a first color indicative of a first respiratory/physiological condition and the second illumination pattern comprises a second, different color indicative of a second respiratory/physiological condition of the subject; and
at least one illumination source functionally associated with the control circuitry and configured to produce the illumination patterns at the same time or sequentially in the gas tube when the first end is connected to the $CO_2$ gas port and the second end is connected to the gas tube, wherein the illumination patterns are characterized by the illumination parameters.

15. The connector of claim 14, further comprising a wireless communication unit, configured to be wirelessly communicatively associated with a control unit of the capnograph and configured to receive from the control unit $CO_2$ sensing data and/or respiratory/physiological conditions assessed, and wherein, based thereon, the control circuitry is configured to determine the illumination parameters.

16. A disposable breath-sampling assembly, configured for use with a capnograph, the breath sampling assembly comprising:
a worn, facially-fitting member configured to be fitted on a nasal/mouth region of a subject;
at least one gas tube fluidly connected, on a first end thereof, to the facially-fitting member, and configured to be detachably connectable on a second end thereof to a gas port of a capnograph;
control circuitry configured to determine one or more illumination parameters based at least on $CO_2$ sensing data obtained by the capnograph to produce a first illumination pattern and a second illumination pattern, wherein the first illumination pattern comprises a first color indicative of a first respiratory/physiological condition and the second illumination pattern comprises a second, different color indicative of a second respiratory/physiological condition of the subject; and
at least one illumination source functionally associated with the control circuitry and configured to produce the illumination patterns at the same time or sequentially in the gas tube when the first end is connected to the $CO_2$ gas port and the second end is connected to the gas tube, wherein the illumination patterns are characterized by the illumination parameters;
wherein the at least one illumination source is located in/on the gas tube or in the facially-fitting member such as to illuminate the gas tube.

17. The breath-sampling assembly of claim 16, further comprising a wireless communication unit, configured to be wirelessly communicatively associated with a control unit of the capnograph and configured to receive from the control unit $CO_2$ sensing data and/or assessed respiratory/physiological conditions, and based thereon to determine the illumination parameters.

18. The breath-sampling assembly of claim 16, wherein the breath sampling assembly is a nasal cannula or oral/nasal cannula and the facially-fitting member comprises at least one nasal prong.

19. The breath-sampling assembly of claim 16, wherein the gas tube comprises at least one optical fiber and wherein the at least one illumination source is configured to project light into the at least one optical fiber and thereby produce the illumination patterns.

* * * * *